(12) United States Patent
Madjarov

(10) Patent No.: US 10,219,849 B2
(45) Date of Patent: Mar. 5, 2019

(54) DEVICE AND SYSTEM FOR SUPPORTING AND APPROXIMATING RIBS

(71) Applicant: THE CHARLOTTE MECKLENBURG HOSPITAL AUTHORITY, Charlotte, NC (US)

(72) Inventor: Jeko Metodiev Madjarov, Charlotte, NC (US)

(73) Assignee: The Charlotte Mecklenburg Hospital Authority, Charlotte, NC (US)

( * ) Notice: Subject to any disclaimer, the term of this patent is extended or adjusted under 35 U.S.C. 154(b) by 437 days.

(21) Appl. No.: 14/902,358

(22) PCT Filed: Jul. 2, 2014

(86) PCT No.: PCT/US2014/045258
§ 371 (c)(1),
(2) Date: Dec. 31, 2015

(87) PCT Pub. No.: WO2015/003061
PCT Pub. Date: Jan. 8, 2015

(65) Prior Publication Data
US 2016/0367301 A1    Dec. 22, 2016

Related U.S. Application Data

(60) Provisional application No. 61/842,676, filed on Jul. 3, 2013, provisional application No. 61/893,420, filed on Oct. 21, 2013.

(51) Int. Cl.
*A61B 17/80* (2006.01)
*A61B 17/82* (2006.01)
(Continued)

(52) U.S. Cl.
CPC ...... *A61B 17/8076* (2013.01); *A61B 17/7053* (2013.01); *A61B 17/8085* (2013.01); *A61B 17/82* (2013.01); *A61B 2017/00004* (2013.01)

(58) Field of Classification Search
CPC . A61B 17/80; A61B 17/8076; A61B 17/8085; A61B 17/82
See application file for complete search history.

(56) References Cited

U.S. PATENT DOCUMENTS

2007/0123883 A1* 5/2007 Ellis .................. A61B 17/8076
606/326
2009/0248090 A1 10/2009 Gordon et al.
(Continued)

FOREIGN PATENT DOCUMENTS

DE            94 17 019 U1      1/1995

OTHER PUBLICATIONS

Notification of Transmittal of the International Search Report and the Written Opinion of the International Searching Authority for corresponding PCT Application No. PCT/US2014/045258, dated Nov. 25, 2014, 18 pages.

*Primary Examiner* — Christopher Beccia
(74) *Attorney, Agent, or Firm* — John P. Zimmer; Nexsen Pruet, PLLC

(57) ABSTRACT

A system for supporting ribs is provided that includes first and second reinforcing members, fasteners, and closure members. Each reinforcing member may be attached to a respective rib via fasteners such that the reinforcing member spans one or more fractures of the ribs. In addition to individually holding the portions of the rib bone together to allow the fracture to heal, however, the reinforcing members may be used on rib pairs such that closure members may be wrapped around or extended between the rib pair in an effort to stabilize the ribs. By providing extended regions configured to receive closure members, healing of the ribs may be promoted and facilitated without creating unnecessary other pain to the patient, as the rounded portions serve to keep the closure members away from the neurovascular bundles associated with the ribs.

11 Claims, 15 Drawing Sheets

(51) Int. Cl.
*A61B 17/70* (2006.01)
*A61B 17/00* (2006.01)

(56) References Cited

U.S. PATENT DOCUMENTS

2009/0312802 A1 12/2009 Dasilva
2010/0331892 A1 12/2010 Fell et al.
2012/0089193 A1 4/2012 Stone et al.

* cited by examiner

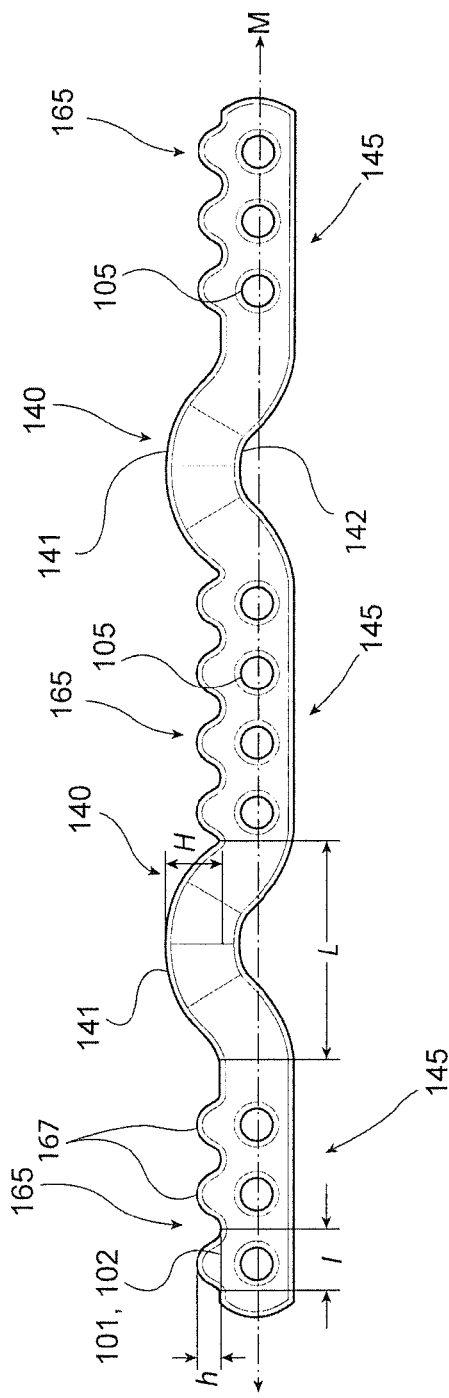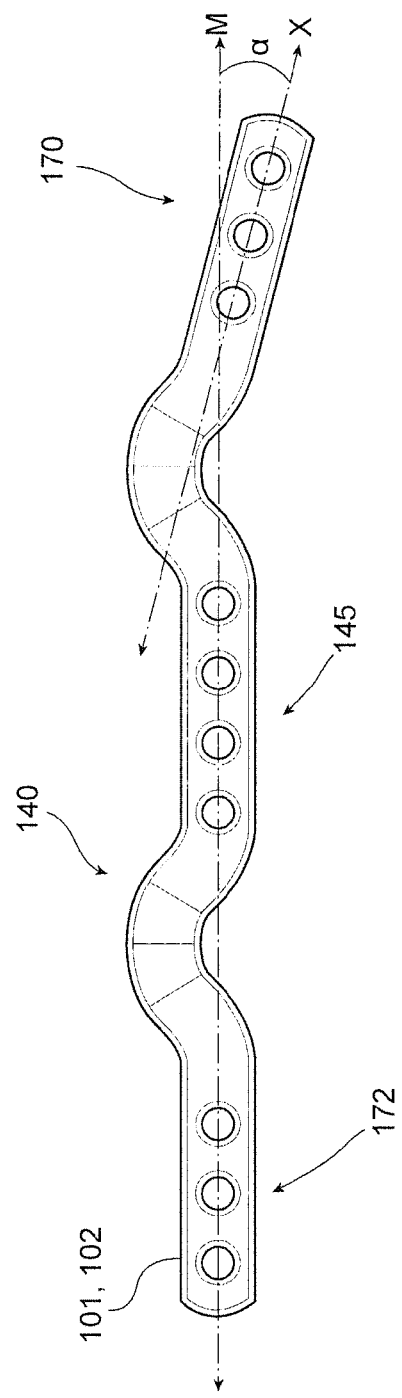
FIG. 6
FIG. 7

DEVICE AND SYSTEM FOR SUPPORTING AND APPROXIMATING RIBS

CROSS REFERENCE TO RELATED APPLICATIONS

This application is a U.S. national stage application under 35 U.S.C. § 371 of International Application No. PCT/US2014/045258, filed on Jul. 2, 2014, which claims priority pursuant to 35 U.S.C. § 119(e) to U.S. Provisional Patent Application Ser. No. 61/842,676, filed on Jul. 3, 2013, and to U.S. Provisional Patent Application Ser. No. 61/893,420, filed on Oct. 21, 2013, each of which is hereby incorporated by reference in its entirety.

FIELD OF THE INVENTION

The present invention relates generally to methods and systems for the fixation of ribs, such as to promote comfortable healing of the ribs during chest wall reconstruction as a result of chest trauma or thoracotomy.

BACKGROUND

The rib cage, or thoracic cage, refers to the bones and cartilage that surround and protect the major organs of the thoracic cavity, including the heart and lungs. In general, a human rib cage consists of the sternum or breastbone, 24 ribs (12 on each side of the sternum), costal cartilage, and 12 thoracic vertebrae. All ribs are attached to the thoracic vertebrae at one end, while, in most humans, only the upper seven pairs of ribs are attached to the sternum via the costal cartilage, which provide the elasticity of the rib cage that is necessary to allow for expansion of the rib cage during respiration. The other ribs (below the upper seven ribs) either join with the costal cartilage of the ribs above them (generally the $8^{th}$ $10^{th}$ ribs) or do not have any connection to the sternum (generally the $11^{th}$ and $12^{th}$ ribs, sometimes called "floating ribs").

The intercostal space refers to the space between each pair of adjacent ribs. Each intercostal space includes a neurovascular bundle, which includes a vein, an artery, and a nerve.

Unfortunately, rib fractures are a common injury. Depending on the severity of the fracture and the number of ribs affected, such injuries can result in respiratory complications, hospitalization, long-term disability, and, in some cases, death. In addition to accidental fracturing of the ribs, in some cases ribs are broken in the process of performing a surgical procedure to provide access to organs such as the heart and lungs (e.g., during a thoracotomy).

Accordingly, there is a need for a system and method for supporting and promoting healing of fractured or broken ribs that is safe, reproducible, simple to administer, and causes the least amount of pain to the patient.

BRIEF SUMMARY OF EXAMPLE EMBODIMENTS

Accordingly, embodiments of a system and method are described that can provide support for fractured ribs to promote healing while minimizing pain and discomfort of the patient. Embodiments of the system include first and second reinforcing members. Each reinforcing member may be configured to be placed on an outer surface of a respective one of a rib pair such that each reinforcing member is laterally disposed on an opposite side, with respect to the other reinforcing member, of an intercostal space that extends between the ribs of the rib pair. At least one of the first reinforcing member or the second reinforcing member may comprise at least one extended region and at least one connecting portion, and the connecting portion may define a plurality of holes. The extended region may include a lateral edge extending away from a midline of the respective reinforcing member.

The system may further include a plurality of fasteners, and each hole of the at least one connecting portion of the first and second reinforcing members may be configured to receive one of the fasteners so as to secure a respective reinforcing member to a corresponding rib. In addition, a plurality of closure members may be provided, with each closure member configured to be extended between the respective rib pair and the first and second reinforcing members secured thereto so as to approximate the respective rib pair. In some embodiments, each extended region may be configured to receive a portion of a corresponding closure member, and the lateral edge of the extended region of the at least one of the first reinforcing member or the second reinforcing member may be configured to clear a neurovascular bundle associated with the respective one of the rib pair so as to minimize discomfort to the patient during healing.

In some cases, the extended region may comprise at least one groove configured to receive the portion of the respective closure member therein. Additionally or alternatively, the extended region may comprise at least one receiving member, which may, for example, include a closure hole, configured to receive the portion of the respective closure member.

Each closure member may comprise two opposing attachment ends and a main body extending therebetween, where each attachment end is configured to engage a corresponding reinforcing member via a respective extended region and the main body is configured to bias the attachment ends towards each other so as to approximate the respective rib pair. Moreover, each closure member may comprise a closure wire configured to be wrapped around the respective rib pair and the first and second reinforcing members secured thereto so as form a closed loop.

In some embodiments, the extended region of the reinforcing members may be an arched region, and the lateral edge may be rounded. The connecting portion of the reinforcing members may comprise at least one scalloped edge configured to receive a portion of a respective closure member. The scalloped edge may be configured to clear a corresponding edge of the respective one of the rib pair such that the respective closure member makes no contact with the corresponding edge of the respective one of the rib pair. In some cases, at least one of a lateral end or a medial end of at least one of the first reinforcing member or the second reinforcing member may be angled away from the midline of the respective reinforcing member.

At least one of the first reinforcing member or the second reinforcing member may comprise an absorbable material. In some cases, at least one of the holes configured for receiving a fastener therethrough may be angled with respect to an axis perpendicular to a surface of the respective rib.

In other embodiments, a reinforcing member for supporting a rib is provided that is configured to be placed on an outer surface of the rib such that the reinforcing member is laterally disposed on an opposite side, with respect to another reinforcing member, of an intercostal space that extends between a pair of adjacent ribs. The reinforcing member may comprise at least one extended region that includes a lateral edge extending away from a midline of the respective reinforcing member. Each extended region may be configured to receive at least one closure member, and each closure member may be configured to be extended between the rib to which the reinforcing member is secured and another rib to which another reinforcing member is secured so as to approximate a respective rib pair. In addition, the reinforcing member may comprise at least one connecting portion, which may define a plurality of holes. Each hole may be configured to receive one of a plurality of fasteners so as to secure the reinforcing member to a corresponding rib. The lateral edge of the extended region may be configured to clear a neurovascular bundle associated with the respective rib so as to minimize discomfort to the patient during healing.

In some cases, the reinforcing member may comprise two extended regions. The extended region may comprise at least one groove configured to receive a portion of the respective closure member therein. In addition or alternatively, the extended region may comprise at least one receiving member configured to receive a portion of a respective closure member.

In some embodiments, the holes configured to receive fasteners therethrough may be defined in the connecting portion. The connecting portion may comprise at least one scalloped edge configured to receive a portion of a respective closure member, and the scalloped edge may be configured to clear a corresponding edge of the respective one of the rib pair such that the respective closure member makes no contact with the corresponding edge of the respective one of the rib pair.

At least one of a lateral end or a medial end of the reinforcing member may be angled away from the midline of the reinforcing member. In some cases, the extended region may be an arched region, and the lateral edge may be rounded. For example, the extended region may have an arched shape, a three-sided arched shape, or an oblique M-shape. Moreover, the reinforcing member comprises absorbable material. The reinforcing member may comprise at least one extension protruding from a respective connecting portion towards an adjacent connecting portion, wherein the at least one extension defines at least one additional hole configured to receive a fastener. In some cases, at least one of the holes configured for receiving a fastener therethrough may be angled with respect to an axis perpendicular to a surface of the respective rib.

In still other embodiments, a closure member for supporting a pair of ribs is provided, where each of the pair of ribs has a reinforcing member secured thereto and where the closure member is configured to extend between the pair of ribs and the respective reinforcing members. The closure member may comprise a first attachment end, a second attachment end, and a main body extending between the first attachment end and the second attachment end. The first attachment end may be configured to engage a corresponding reinforcing member, and the second attachment end opposite the first attachment end and configured to engage a corresponding reinforcing member. Each attachment end may be configured to be secured to the corresponding reinforcing member, and the main body may be configured to bias the first and second attachment ends towards each other so as to approximate the respective rib pair.

In some cases, one of the first or second attachment ends may comprise an anchor configured to engage the corresponding reinforcing member. At least one of the first or second attachment ends may be configured to be secured to the corresponding reinforcing member so as to adjust a length of the closure member from an engagement point of one reinforcing member to an engagement point of the other reinforcing member. Additionally or alternatively, at least one of the first or second attachment ends may be configured to be passed through a receiving member defined in the corresponding reinforcing member, wherein the receiving member comprises a closure hole.

The at least one of the first or second attachment ends may be configured to allow a free end of the respective attachment end to be wrapped around another portion of the respective attachment end so as to secure the respective attachment end to the corresponding reinforcing member. In some cases, the at least one of the first or second attachment ends may be configured to allow a free end of the respective attachment end to be wrapped around another portion of the respective attachment end so as to secure the respective attachment end to the corresponding reinforcing member. Moreover, in some cases, the at least one of the first or second attachment ends comprises a locking feature configured to receive a free end of the respective attachment end in a first direction and to prevent movement of the free end in a second direction so as to secure the respective attachment end to the corresponding reinforcing member.

In some embodiments, at least one of the first or second attachment ends defines threads may be configured to engage corresponding threads of a fastener, wherein engagement of the fastener with the at least one of the first or second attachment ends serves to secure the respective attachment end to the corresponding reinforcing member. In some cases, the main body may comprise an expansion feature that is configured to allow a distance between the pair of ribs to increase and decrease due to respiration while biasing the first and second attachment ends towards each other. Moreover, the closure member may be coated with a polymer, and at least the main body may comprise nitinol or titanium.

In still other embodiments, a method of supporting a pair of ribs is provided that comprises the steps of attaching a first reinforcing member to an outer surface of a first one of a rib pair; attaching a second reinforcing member to an outer surface of a second one of the rib pair such that each reinforcing member is laterally disposed on an opposite side, with respect to the other reinforcing member, of an intercostal space that extends between the ribs of the rib pair; applying a plurality of closure members to the reinforcing members; and securing ends of each closure member with respect to the reinforcing members to approximate the ribs. At least one of the first reinforcing member or the second reinforcing member may comprise at least one extended region and at least one connecting portion, where the extended region includes a lateral edge extending away from a midline of the respective reinforcing member, and where at least one of the closure members is applied to the lateral edge of the extended region so as to clear a neurovascular bundle associated with the respective one of the rib pair and minimize discomfort to the patient during healing.

In some cases, the closure members may comprise closure wires, and the method may further comprise wrapping the closure members around the respective rib pair and the first and second reinforcing members secured thereto so as to form a closed loop. Additionally or alternatively, each closure member may comprise two opposing attachment ends and a main body extending therebetween, and the method may further comprise engaging each attachment end with a corresponding reinforcing member via a respective extended region such that the closure members extend between the ribs of the rib pair on an outer side of the ribs, only, with the main body configured to bias the attachment ends towards each other so as to approximate the respective rib pair.

BRIEF DESCRIPTION OF THE DRAWINGS

Figure 1:
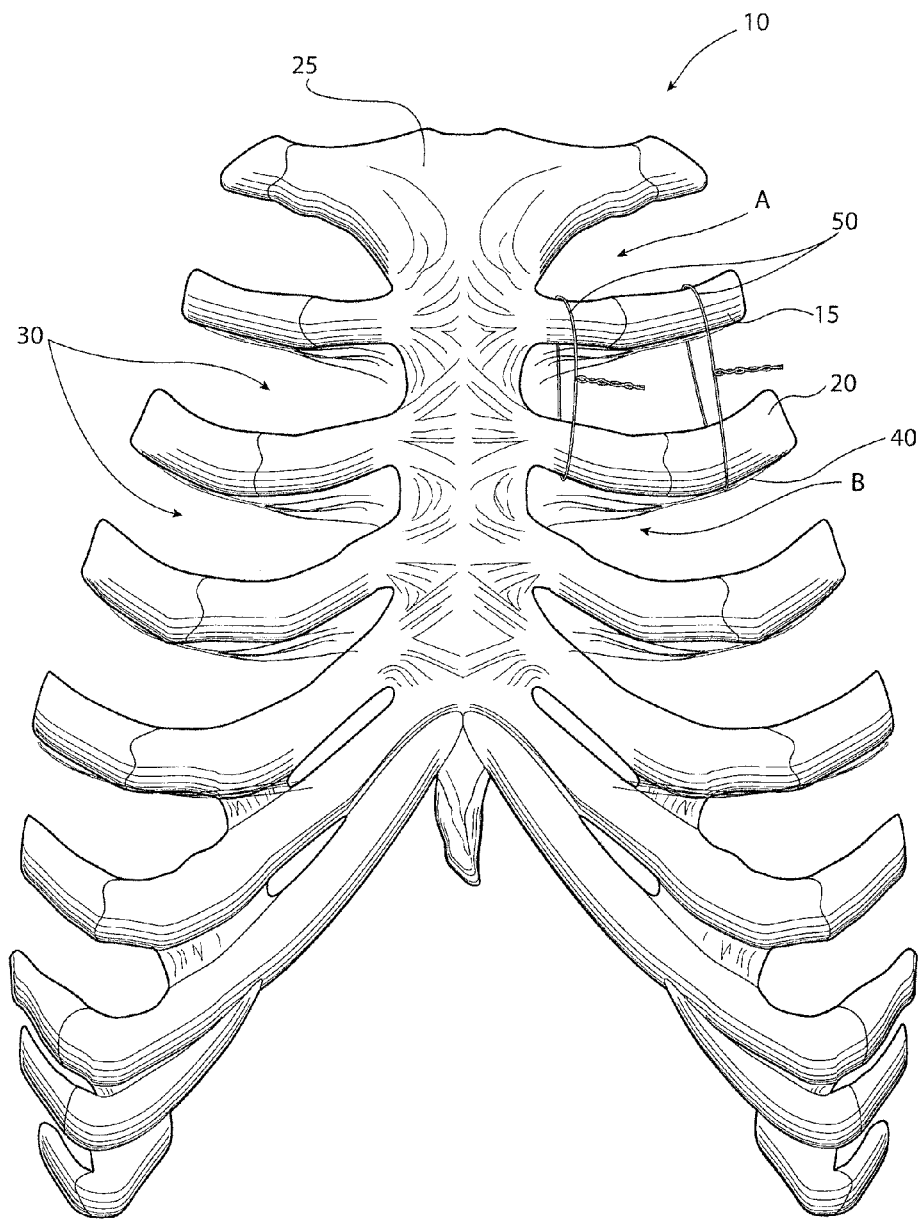
Figure 2:
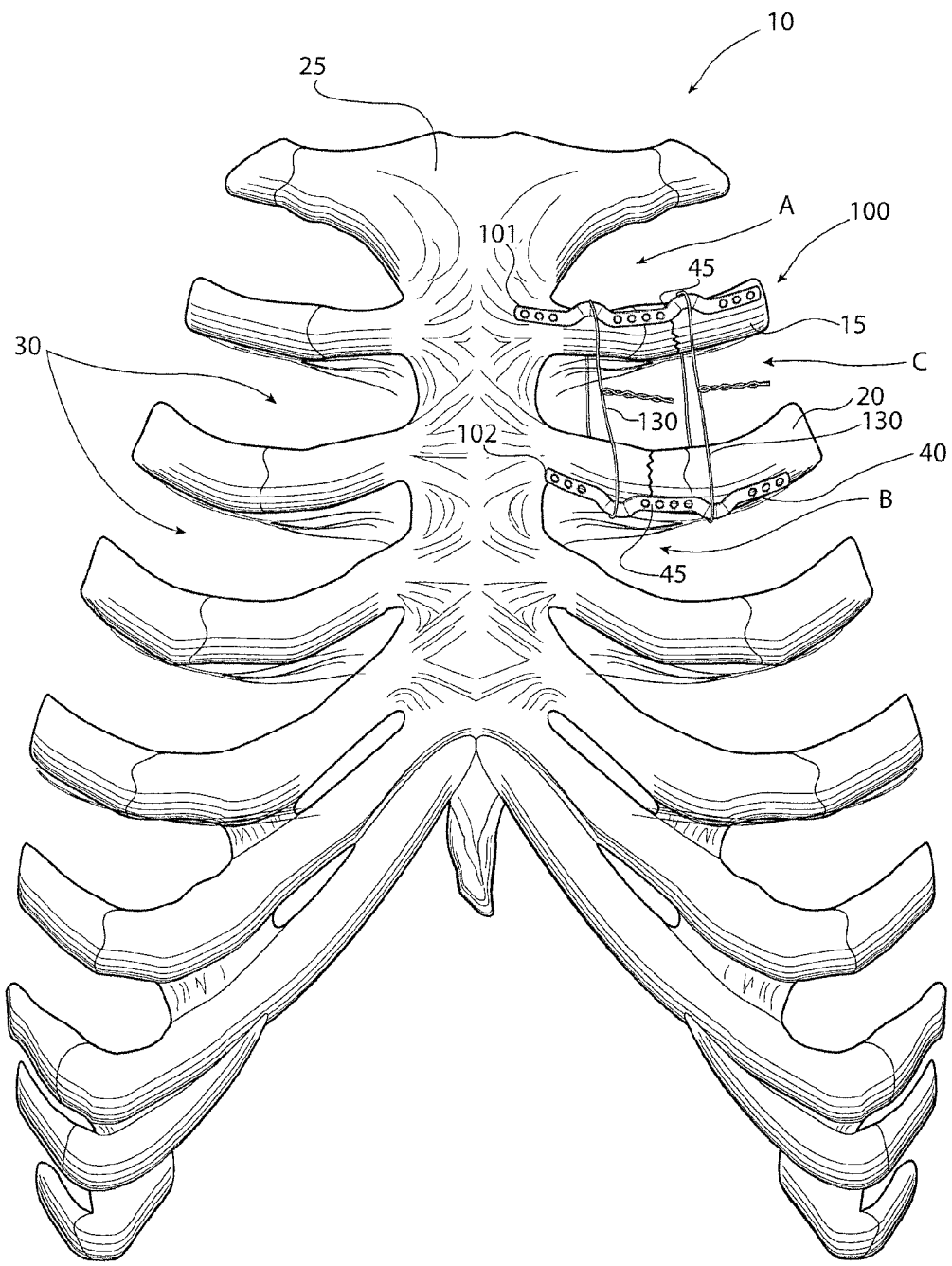
Figure 3:
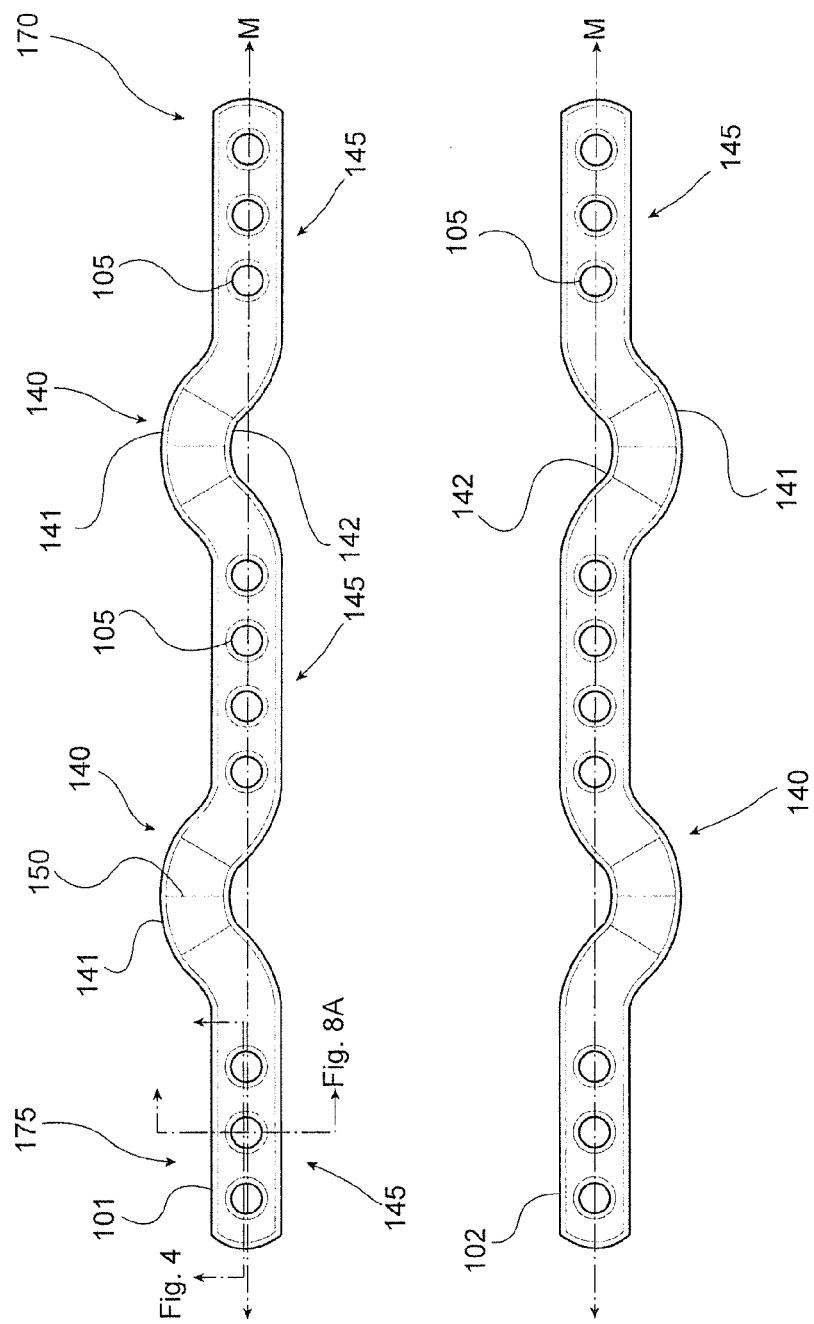
Figure 4:
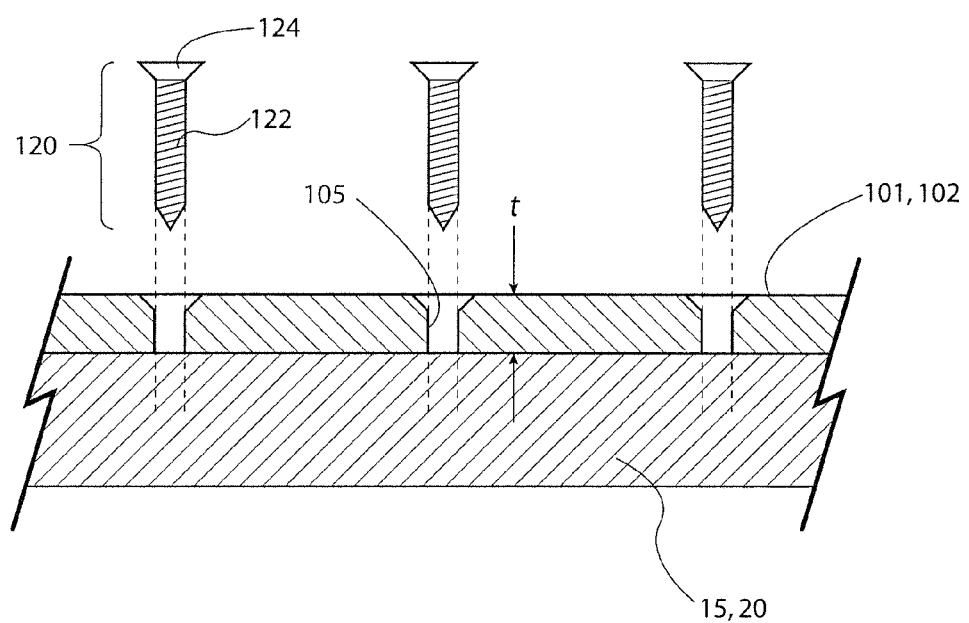
Figure 5:
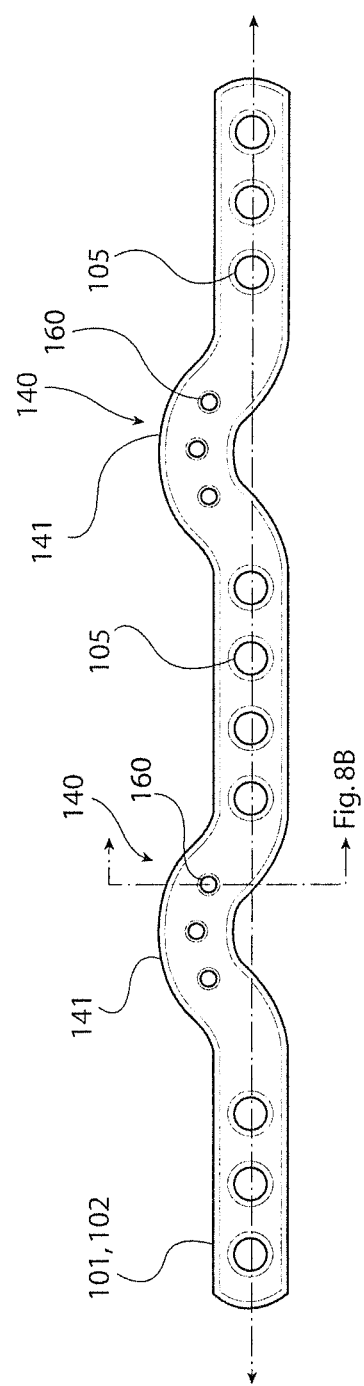
Figure 8A:
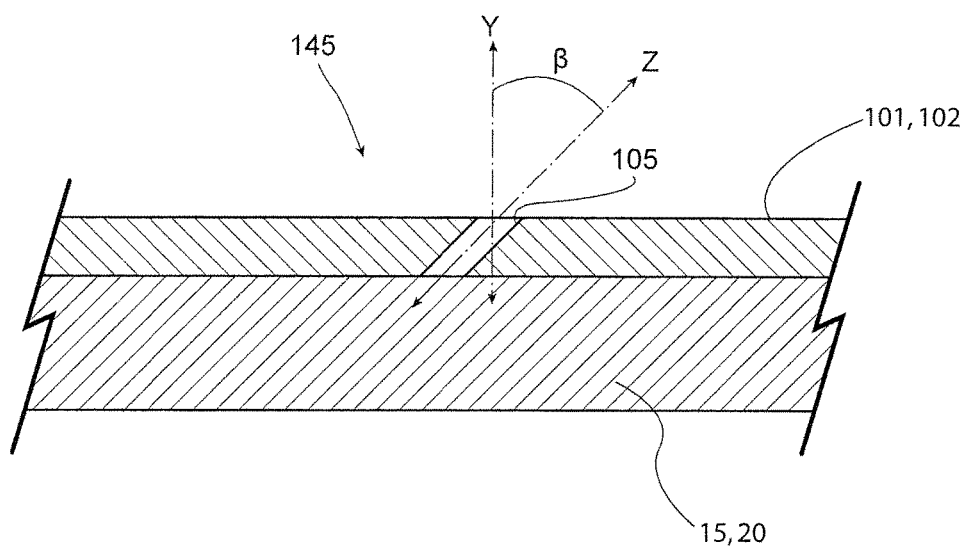
Figure 8B:
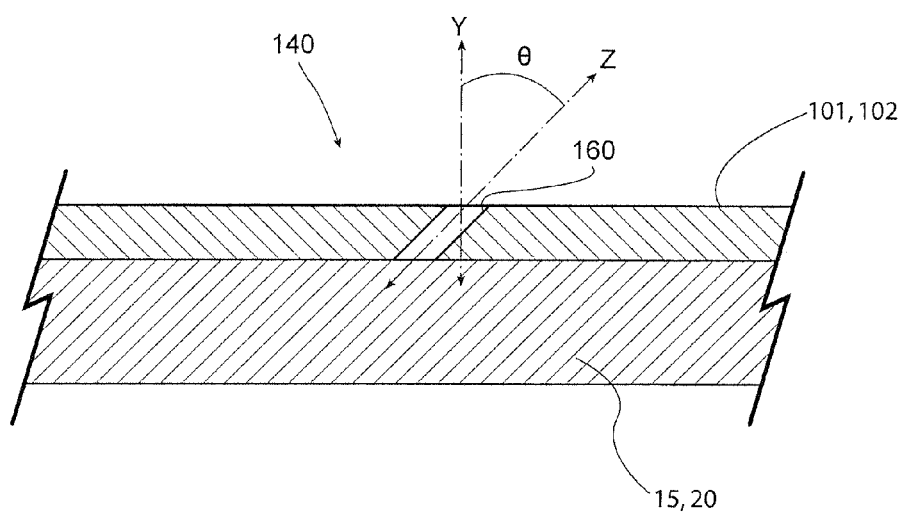
Figure 9:
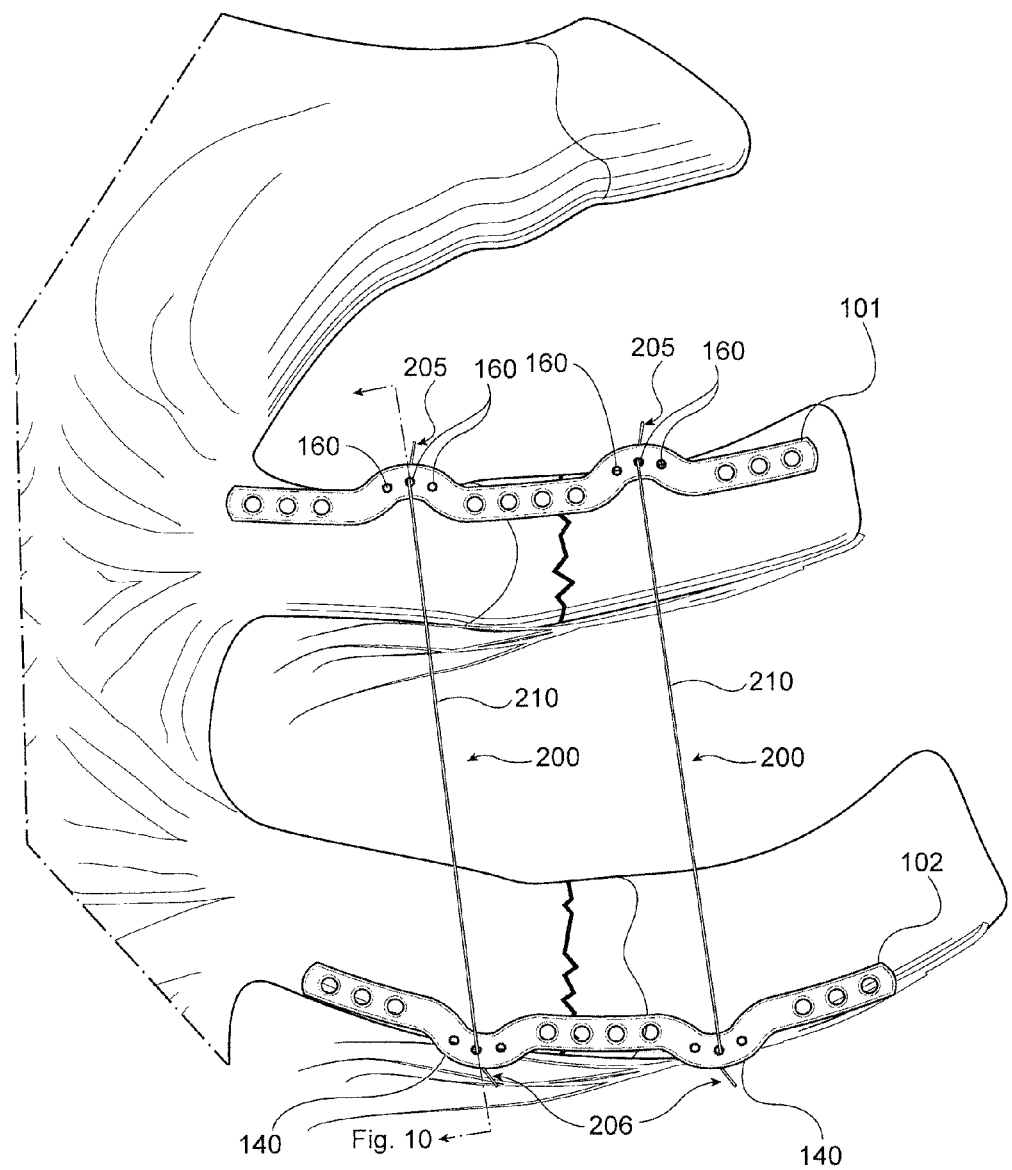
Figure 10:
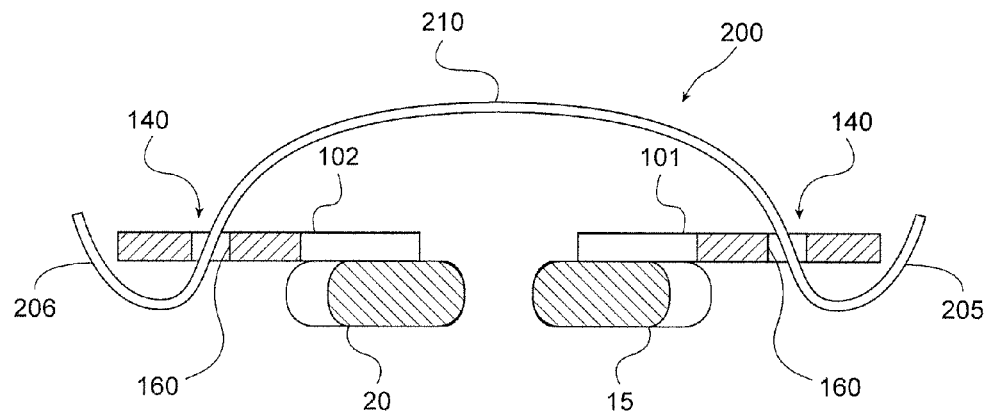
Figure 11:
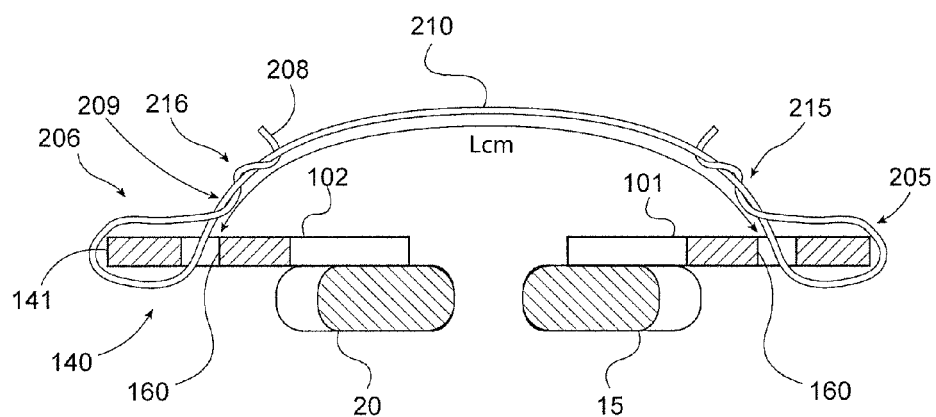
Figure 12:
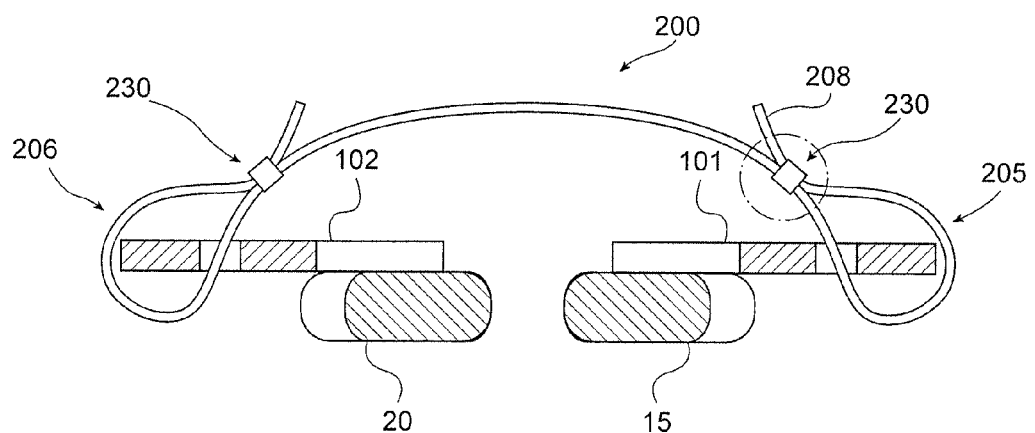
Figure 12A:
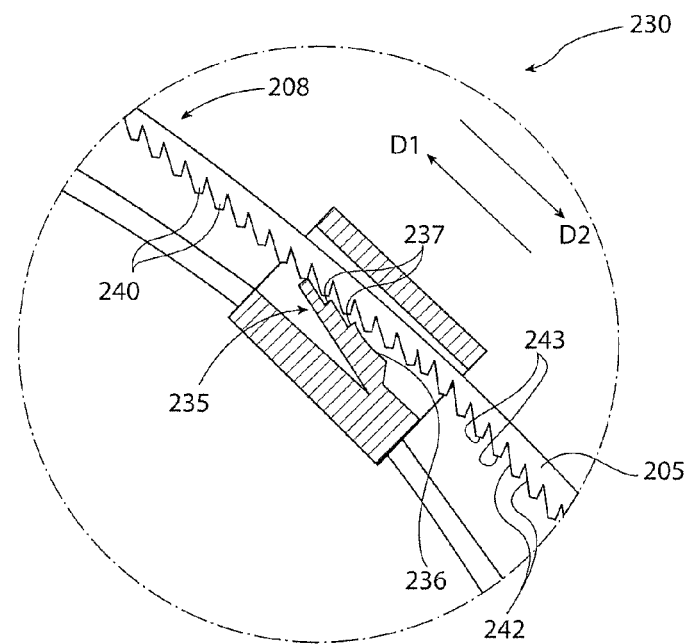
Figure 13:
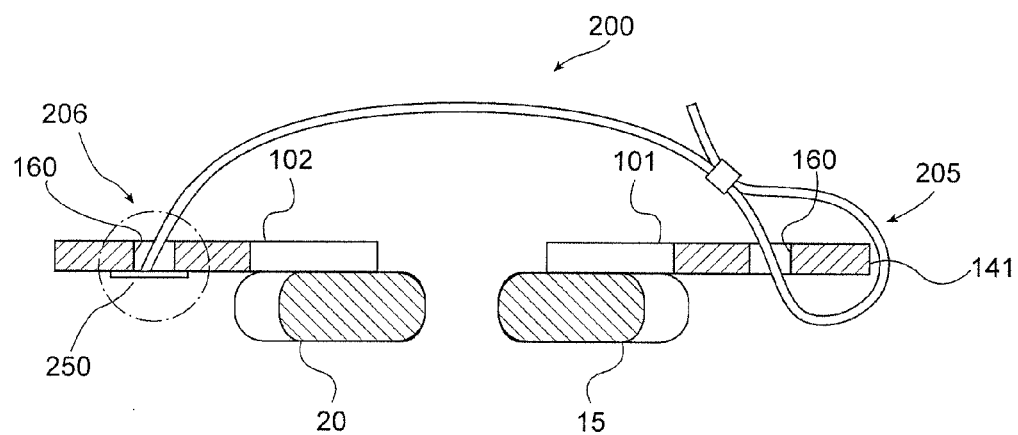
Figure 13A:
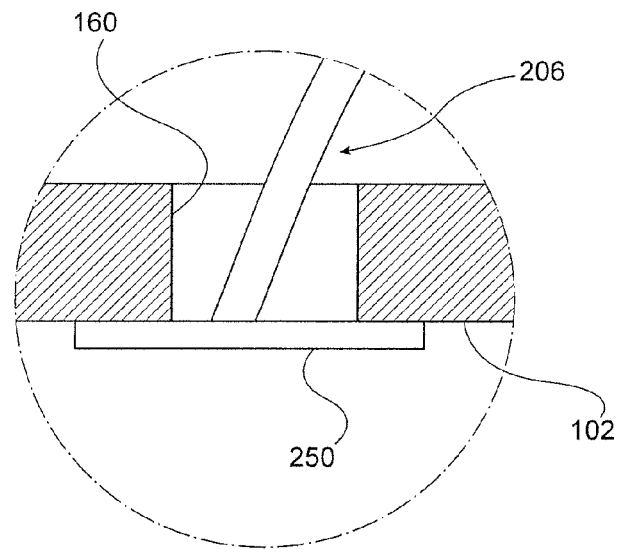
Figure 14A:
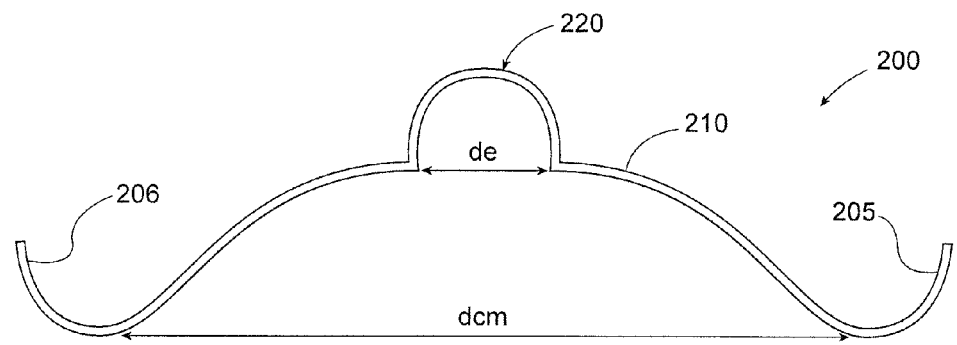
Figure 14B:
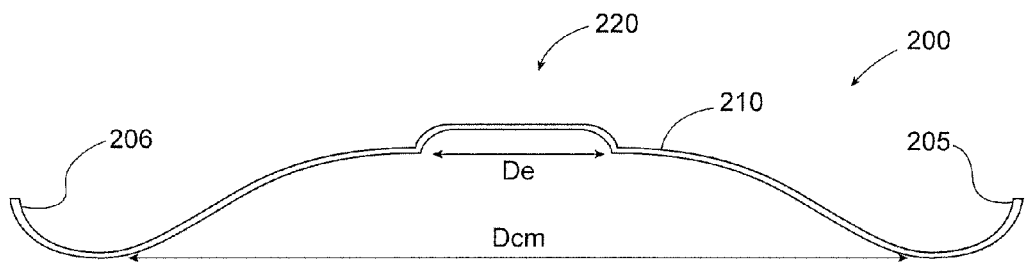
Figure 15:
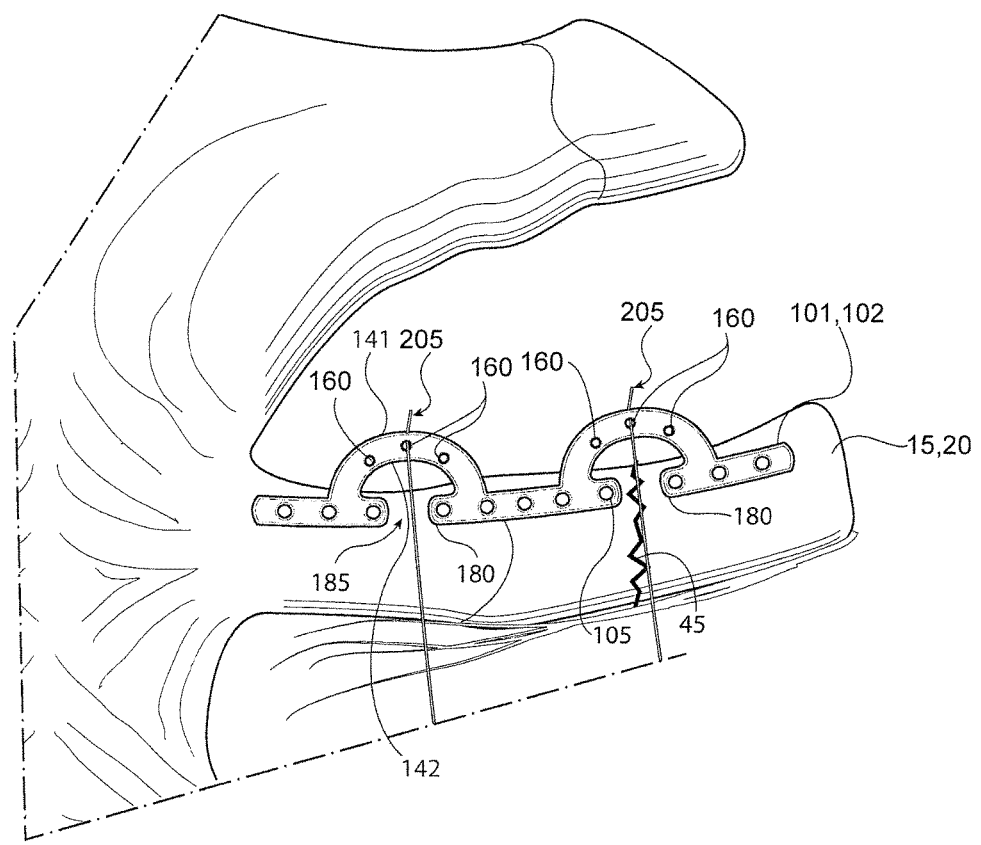
Figure 16:
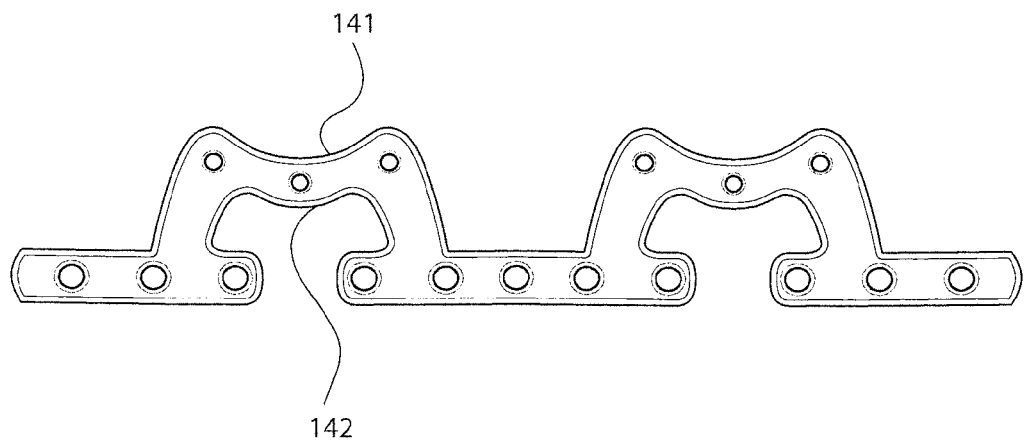
Figure 17:
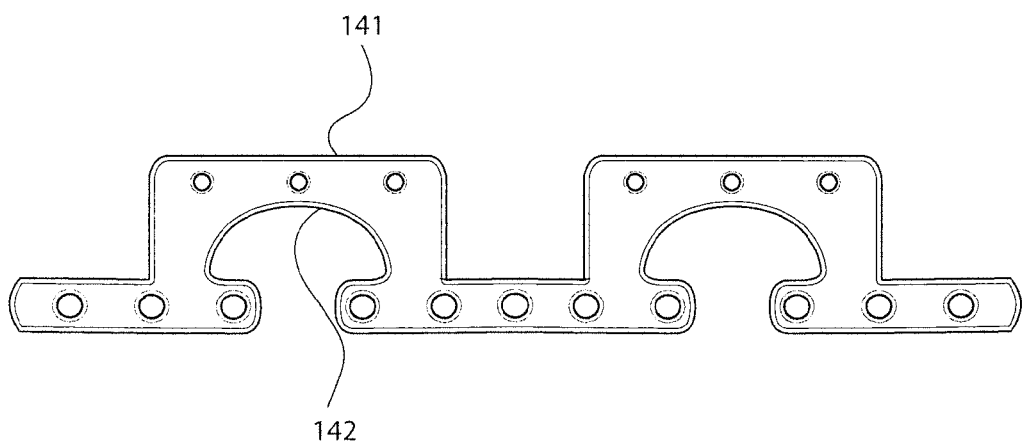

Having thus described the invention in general terms, reference will now be made to the accompanying drawings, which are not necessarily drawn to scale, and wherein:

FIG. 1 shows a schematic representation of a rib cage with sutures applied to a pair of ribs;

FIG. 2 shows a schematic representation of a system for supporting and approximating ribs in accordance with an exemplary embodiment of the present invention;

FIG. 3 shows reinforcing members of the system for supporting and approximating ribs in accordance with an exemplary embodiment of the present invention;

FIG. 4 shows a partial cross-section of one of the reinforcing members of FIGS. 2 and 3 in accordance with an exemplary embodiment of the present invention;

FIG. 5 shows a reinforcing member of a system for supporting and approximating ribs in accordance with another exemplary embodiment of the present invention;

FIG. 6 shows a reinforcing member of a system for supporting and approximating ribs in accordance with another exemplary embodiment of the present invention;

FIG. 7 shows a reinforcing member of a system for supporting and approximating ribs in accordance with another exemplary embodiment of the present invention;

FIG. 8A shows a partial cross-section of one of the reinforcing members of FIGS. 2 and 3 in accordance with another exemplary embodiment of the present invention;

FIG. 8B shows a partial cross-section of one of the reinforcing members of FIGS. 2 and 5 in accordance with another exemplary embodiment of the present invention;

FIG. 9 shows a top view of a pair of reinforcing members with closure members applied thereto in accordance with another exemplary embodiment of the present invention;

FIG. 10 shows a side view of two reinforcing members with a closure member passing through respective closure holes in accordance with another exemplary embodiment of the present invention;

FIG. 11 shows a side view of two reinforcing members with a closure member having attachment ends that wrap around a portion of the closure members to secure the closure members to the reinforcing members in accordance with another exemplary embodiment of the present invention;

FIG. 12 shows a side view of two reinforcing members with a closure member having attachment ends including locking features in accordance with another exemplary embodiment of the present invention;

FIG. 12A shows a close-up view of the locking feature of FIG. 12;

FIG. 13 shows a side view of two reinforcing members with a closure member having an attachment end with an anchor in accordance with another exemplary embodiment of the present invention;

FIG. 13A shows a close-up view of the anchor of FIG. 13;

FIG. 14A shows a closure member having an expansion feature in a first position in accordance with another exemplary embodiment of the present invention;

FIG. 14B shows a closure member having an expansion feature in a second position in accordance with another exemplary embodiment of the present invention;

FIG. 15 shows a top view of a reinforcing member in accordance with another exemplary embodiment of the present invention;

FIG. 16 shows a reinforcing member having an oblique M-shape in accordance with another exemplary embodiment of the present invention; and FIG. 17 shows a reinforcing member having a three-sided arch shape in accordance with another exemplary embodiment of the present invention.

DETAILED DESCRIPTION

Some embodiments of the present invention will now be described more fully hereinafter with reference to the accompanying drawings, in which some, but not all, embodiments of the invention are shown. Indeed, various embodiments of the invention may be embodied in many different forms and should not be construed as limited to the embodiments set forth herein; rather, these embodiments are provided so that this disclosure will satisfy applicable legal requirements. Like reference numerals refer to like elements throughout.

As used herein, the terms "lateral" and "laterally" refer to a location of an anatomical structure (such as a bone) or movement in a direction towards a point that is farthest from the center of the respective structure. Similarly, the terms "medial" and "medially" refer to a location or movement towards a point closest to the center of the respective structure. The terms "upper" and "lower" are used for explanatory purposes in the examples provided below, where the term "upper" indicates a position or structure that is located toward the head of a human patient with respect to another structure and the term "lower" indicates a position or structure that is located toward the feet of a human patient wither respect to another structure. Furthermore, although each example described herein refers to devices, systems, and methods for supporting ribs such as for chest wall reconstruction, embodiments of the described invention may be used to hold together and/or approximate other bones.

Referring now to FIG. 1, a schematic representation of a rib cage 10 showing a pair of adjacent ribs 15, 20 to be supported is shown. The subject ribs 15, 20 may be, for example, the $2^{nd}$ and $3^{rd}$ ribs of a human patient in which chest wall reconstruction is required as a result of blunt trauma to the chest.

As noted above, all ribs are attached to the thoracic vertebrae (not shown), while, in most humans, only the upper seven pairs of ribs are attached to the sternum 25 via the costal cartilage. Each intercostal space 30 (i.e., the space between adjacent pairs of ribs) generally includes a neurovascular bundle 40, which includes a vein, an artery, and a nerve.

In conventional procedures for addressing broken ribs (e.g., as a result of chest trauma or due to a thoracotomy), a conventional fixation system may be used that includes a plate designed to be fastened to the periosteum of the rib (i.e., the rib surface) using screws so as to span the fracture or fractures of the particular rib and hold the rib together to promote healing. In conventional rib fixation systems, however, each rib is splinted independently of other ribs. For example, adjacent ribs that require fixating, using conventional methods, must be splinted individually. The lack of support with respect to the rest of the rib cage using conventional methods often causes a recovering patient to experience pain and discomfort during the healing process, such as during respiration (e.g., when the rib cage expands and contracts) and when coughing, sneezing, etc.

Approximating the ribs (e.g., stabilizing two ribs by holding them to each other) using conventional methods is generally not favored, as the approximation may cause more damage to the rib bones and even more pain and discomfort to the patient. For example, use of metal wires 50 (as shown in FIG. 1) to approximate a pair of ribs by passing the wires through the intercostal space A above the upper rib 15 and the intercostal space B below the lower rib 20 and securing the wires together (e.g., via twisting or tying of the ends) to hold two ribs to each other may result in the wires contacting or otherwise interfering with neurovascular bundles near the ribs being approximated. In particular, the neurovascular bundle 40 located proximate the lower edge of the lower rib 20 may be affected (e.g., pinched or rubbed), thereby creating discomfort or, in some cases, severe pain for the patient. Such discomfort or pain is often amplified as the rib cage expands and contracts with each breath that the patient draws into the lungs. Moreover, in some cases, because the wires are disposed directly on the bone of the subject ribs 15, 20, there is often a risk that forces applied to the ribs, such as by inhaling and exhaling or from the patient's movement in performing everyday tasks, will cause the wire to cut into the bone in the various locations where the wires contact the bone. This may, at best, cause the patient to suffer from pain and discomfort and may, at worst, cause serious damage to the rib cage, such as additional fractures of the sternum where the wires have cut all the way through the bone.

Accordingly, and as illustrated in FIG. 2, a system 100 for supporting ribs is provided that includes first and second reinforcing members 101, 102, fasteners 120 (shown in FIG. 4), and closure members 130. As described in greater detail below, each reinforcing member 101, 102 is configured to be attached to a respective rib 15, 20 via the fasteners 120 such that the reinforcing member spans one or more fractures 45 of the ribs. Each reinforcing member 101, 102 can be used individually, such as to span fractures and promote healing on two different ribs in different locations on the rib cage (e.g., non-adjacent or adjacent ribs). In addition to holding the portions of the rib bone together to allow the fracture to heal, however, the reinforcing members 101, 102 may be used together in an effort to stabilize the ribs, as described below.

In this regard, embodiments of the reinforcing members 101, 102 may be configured to be installed such that closure members 130 can be applied to two adjacent ribs 15, 20 that have been reinforced with the reinforcing members. The configuration of the reinforcing members 101, 102 is such that the closure members 130 are disposed away from the neurovascular bundles 40 near the ribs and/or do not make direct contact with the bone. By applying closure members 130 as illustrated and described below, the two ribs 15, 20 may be held together and can support each other such that movement of the ribs (e.g., during respiration or other movements) is limited and the ribs are allowed to heal. At the same time, the configuration of the reinforcing members 101, 102 minimizes the pain experienced by the patient as the closure members 130 are not in direct contact and/or do not interfere with the rib structure or nearby neurovasculature.

With reference to FIG. 2, in one embodiment, the reinforcing members 101, 102 may be made of titanium alloy or other biocompatible metal or other material, such as, for example, absorbable materials including absorbable alpha esters such as polylactide and polydioxanone polymers. The closure members 130 may, for example, be metal wires as described above, cables, or heavy sutures, such as pediatric or regular sternal sutures ranging in diameter from 0.05 mm to 0.5 mm or larger and made of stainless steel or other biocompatible materials (including absorbable and non-absorbable materials).

Each reinforcing member 101, 102 may be configured to be placed on an outer surface of a respective one of a rib pair 15, 20 (e.g., spanning one or more rib fractures as needed) such that each reinforcing member is laterally disposed on an opposite side, with respect to the other reinforcing member, of an intercostal space C that extends between the ribs of the rib pair.

Turning to FIGS. 3 and 4, a number of holes 105 may be defined in each reinforcing member 101, 102, with each hole configured to receive one of the fasteners 120 so as to secure a respective reinforcing member to a corresponding rib 15, 20. In some embodiments, for example, the holes 105 may be defined in one or more of the connecting portions 145 of the reinforcing members 101, 102, as illustrated. The number of holes 105 provided in the connecting portions 145 may vary. For example, in some cases, 2, 3, or 4 holes 105 may be provided in the connecting portions 145. Moreover, the number of holes 105 in each connecting portion 145 of a particular reinforcing member 101, 102 may be different. In the embodiment depicted in FIG. 3, for example, the connecting portions 145 provided at either end 170, 175 of the reinforcing plates 101, 102 each defines 3 holes 105, whereas the connecting portion 145 provided between the extended regions 140 (e.g., in the central area of the reinforcing members 101, 102) defines 4 holes 105.

Moreover, in some embodiments, the number of holes 105 provided in each reinforcing member 101, 102 may be greater than the number of holes needed to effect securement of the respective reinforcing member to the corresponding rib 15, 20. For example, although holes 105 may be spaced approximately 2 cm apart, the surgeon may choose to install a fastener 120 in every other hole 105, leaving some of the holes empty. In other cases, the surgeon may decide to install two or three fasteners 120 in a medial end 175 of each reinforcing member 101, 102 (e.g., closer to the sternum) and may install fewer fasteners in a lateral end 170 of the reinforcing members. The location of the fasteners 120 with respect to each reinforcing member 101, 102 may be based on the surgeon's preferences, the condition of the bone (e.g., bone density or other defects in the bone), the condition of surrounding tissue, and/or other factors.

The fasteners 120 may be, for example, bone screws that have a shaft portion 122 and a head portion 124. The bone screws, which may be self-locking screws, may range from about 5 mm to 17 mm long to properly engage the ribs 15, 20 without creating a risk of puncture of any organs or tissue located behind the ribs. The shaft portion 122 may be sized to have an outer diameter substantially equal to or slightly larger than the diameter of the hole 105, such that the fastener forms a tight fit with the reinforcing member 101, 102. In some cases, the diameter of the holes 105 may range from approximately 3 mm to approximately 9 mm. In this regard, the bone of the respective rib 15, 20 may be pre-drilled in some cases to receive the fastener 120. In other cases, however, insertion of the fastener 120 through the hole 105 and into the underlying bone may serve to secure the fastener to the bone of the respective rib 15, 20 without pre-drilling. The holes 105 in some embodiments may be counterbored, such that the head portion 124 of the fastener 120 is substantially flush with the outer surface of the reinforcing member 101, 102 or recessed within the reinforcing member.

With reference to FIG. 3, at least one of the first reinforcing member 101 or the second reinforcing member 102 may comprise at least one extended region 140 and at least one connecting portion 145. The extended region 140 may include a lateral edge 141 extending away from a midline M of the respective reinforcing member 101, 102. The lateral edge 141 may, in some cases, be rounded, as depicted in the figures. In some embodiments the inner edge 142 of the extended region 140 may also be a rounded edge, as illustrated, whereas in other embodiments the inner edge and/or the lateral edge 141 may not be rounded and may, instead, extend in a linear fashion between either end of the extended region.

Each extended region 140 may be configured to receive a portion of a corresponding closure member. Thus, in some embodiments, the lateral edge 141 of the extended region 140 of the at least one of the first reinforcing member 101 or the second reinforcing member 102 may be configured to clear a neurovascular bundle 40 associated with the respective one of the rib pair 15, 20 so as to minimize discomfort to the patient during healing. In addition to keeping the closure members 130 that are received via the lateral edge 141 away from the neurovascular bundles 40, the shape of the extended region 140 (which may be, for example, arched in some embodiments, as shown) may provide additional strength to the respective reinforcing member 101, 102, especially in the location of the extended region, to support the localized forces that are applied to the reinforcing member via the closure members 130.

In some cases, the extended region 140 may comprise at least one groove 150 configured to receive a portion of a respective closure member 130 therein, as illustrated in FIG. 3. In the depicted embodiment, three grooves 150 are provided in each extended region 140, and each groove extends between the inner edge 142 and the lateral edge 141 of the extended region. In other embodiments, however, fewer or more grooves may be provided. In addition, the groove 150 may only be provided proximate the lateral edge 141. Moreover, the lateral edge 141 may be bezeled (e.g., have a reduced thickness as compared to the inner edge 142) to further facilitate receipt of the closure member 130 and provide for a lower profile of the system 100.

In still other embodiments, as shown in FIG. 5, the extended region may comprise one or more closure holes 160 that are configured to receive a portion of the respective closure member 130 therethrough for aiding in keeping the closure members 130 from moving with respect to the reinforcing member 101, 102 during installation and following installation (e.g., to keep the closure members in place with respect to the reinforcing member). For example, three closure holes 160 may be provided, as shown, and one or more of the closure holes may be provided with a closure member 130, as deemed necessary by the surgeon for fixating the ribs 15, 20. Moreover, in some cases, the closure holes 160 may be provided in conjunction with the grooves 150, such that the surgeon may choose which of the two methods to employ to keep the system 100 in place considering the condition of the patient and other surgical variables and considerations.

The reinforcing members 101, 102 may range in length from approximately 2 inches long to approximately 10 inches long, depending on the extent and type of damage to the rib (e.g., the number and location of fractures) and other considerations. Accordingly, although the embodiments depicted in the figures include two extended regions 140 and three connecting portions 145, depending on the total length of the reinforcing member 101, 102, additional or fewer extended regions 140 and connecting portions 145 may be provided, such as two, three, or four extended regions. For example, in some embodiments, a plurality of extended regions 140 may be provided. For example, an extended region 140 may be provided for every 2 inches of reinforcing member, such that a 4-inch long reinforcing member would include two extended regions (as depicted, for example, in FIG. 3). In this regard, in some embodiments, the length of an extended region 140 may be approximately 0.5 cm to approximately 3 cm, while the length of a connecting portion 145 may be approximately 2 cm to approximately 6 cm. Turning now to FIG. 6, in some embodiments, the connecting portion 145 may comprise at least one scalloped edge 165 along its outer edge that is configured to receive a portion of a respective closure member. The scalloped edge 165 may define a number of scallops 167, or curved portions, that extend away from the midline M of the respective reinforcing member 101, 102. Each scallop 167 may be sized smaller than the corresponding lateral edge 141 of the extended region 140, such that, for example, the length l of the scallop is smaller than the length L of the lateral edge, and the height h of the scallop is smaller than the height H of the lateral edge. In some cases, the length l of a scallop may be approximately 0.25 cm to approximately 0.75 cm, whereas the length L of the lateral edge may be approximately 0.5 cm to approximately 3 cm. Similarly, the height h of a scallop may be approximately 0.25 cm to approximately 0.75 cm, whereas the height H of the rounded outer edge may be approximately 0.5 cm to approximately 1.5 cm.

Thus, in some embodiments, the scalloped edge 165 may be configured to clear a corresponding edge of the respective one of the rib pair 15, 20 such that a closure member may be wrapped around the connecting portion 145 without making contact with the corresponding edge of the respective one of the rib pair. In other words, in the event that the surgical procedure requires that a closure member be disposed in the connecting portion 145, in addition to or instead of in the extended region 140, the scalloped edge 165 that is provided may allow for the closure member to be moved far enough away from the edge of the rib to which the reinforcing member is fastened so as to be clear of the corresponding neurovascular bundle, as described above with respect to the extended region.

With reference to FIG. 4, the reinforcing members 101, 102 may be configured to have a thickness t of between approximately 1 mm to approximately 3 mm. The thickness of a reinforcing member 101, 102 may depend on the length of the reinforcing member, the number of extended regions 140 and connecting portions 145, and/or the number of holes 105, among other considerations, such that a thickness t may be selected that imparts pliability or flexibility allows the reinforcing members to better conform to the curvature of the surface of the ribs 15, 20 to which the respective reinforcing member is fastened, while at the same time providing the appropriate amount of strength to support the closure members 130 applied thereto and promote healing of the bone fractures while minimizing the pain and discomfort experienced by the patient, as described herein.

In still other embodiments, a lateral end 170 (e.g., the end farthest from the sternum when installed) of at least one of the first reinforcing member 101 or the second reinforcing member 102 may be angled away from the midline M of the respective reinforcing member, as shown in FIG. 7. In some cases, the lateral end 170 may be angled away from midline M in a direction that is opposite of the direction in which the extended region 140 extends (as shown in FIG. 7), whereas in other cases the lateral end 170 is angled such that it lies on the same side of the midline M as the extended region (not shown). An axis X of the lateral end 170 may, for example, form an angle α with the midline M of between approximately 3° and approximately 10°, such as in the range of approximately 5° and 7°.

The angle α may be selected, for example, so as to allow the reinforcing member 101, 102 to be bent to conform more closely to the natural curvature of the rib 15, 20 to which it is to be applied. In other words, depending on the length of the reinforcing member 101, 102, the surgeon may choose to bend the reinforcing member to match the curvature of the rib 15, 20 to which it will be applied (e.g., bending the reinforcing member in a direction into or out of the page to match the curvature of the surface of the rib). In so doing, due to the angle α of the lateral end 170, the lateral end may approach the midline M as the reinforcing member 101, 102 is bent, thereby achieving a better fit with the underlying rib 15, 20 than a reinforcing member that does not have an angled lateral end. Moreover, in some embodiments, both the lateral end 170 and a medial end 172 of the reinforcing member 101, 102 may be angled to the same or similar degree (not shown). In other embodiments, however, the reinforcing members 101, 102 may be pre-bent (e.g., as part of a manufacturing process), with longer reinforcing members having a degree of curvature that is greater than shorter reinforcing members. For example, a reinforcing member 101, 102 that is 2 inches long may not need to be pre-bent or bent on-site, whereas a reinforcing member that is 6 inches long may need to be bent (pre-bent or bent by the surgeon) to more closely conform to the curvature of the rib.

As a result of the curvature of the reinforcing members 101, 102, when the reinforcing members are attached to the respective ribs 15, 20 via the fasteners 120, there may be a greater area of contact between the surface of the reinforcing members and the adjacent surface of the ribs. Better contact, in turn, may result in fewer localized forces and less stress on the reinforcement members and the areas of the bone surrounding the fasteners 120, as the reinforcing members will have a lesser tendency to pull the fasteners out of the bone as compared to reinforcing members that are not curved.

In some cases, the extended regions 140 may be configured to be more malleable as compared to the connecting portions 145 so as to allow a surgeon to bend the reinforcing member 101, 102 to achieve a particular angle α with respect to the midline M (shown in FIG. 7). For example, different alloys of titanium may be used to enable the extended regions 140 to be more malleable. Additionally or alternatively, the shape of the extended region 140 may be selected to allow the surgeon to bend the reinforcing member 101, 102 to achieve the desired angle to conform the reinforcing member to the curvature of the particular rib. For example, in some cases, the extended regions 140 may have an oblique M shape, as shown in FIG. 16, to facilitate bending. In this way, the surgeon may be able to apply the appropriate degree of angling α to match the configuration of the patient's ribs to which the reinforcing member is to be applied.

In this regard, with reference to FIG. 15, in some embodiments the reinforcing member 101, 102 may include an extension 180 in the vicinity of the extended regions 140 that includes one or more additional holes 105 configured for receiving a fastener therethrough. For example, as depicted in FIG. 15, first and second extensions 180 may protrude from the connecting portions 145 on either side of the extended region 140 therebetween towards each other, leaving a gap 185. The gap 185 may allow the surgeon to apply the appropriate degree of angling a via the extended region 140, as described above, while at the same time providing additional areas for the reinforcing member 101, 102 to be secured to the underlying bone. In this way, the reinforcing member 101, 102 may be securely attached to the bone 15, 20, even in a case in which the fracture 45 is in the vicinity of the extended region 140.

In still other embodiments, at least one of the holes 105 configured for receiving a fastener therethrough may be angled with respect to an axis Y perpendicular to a surface of the respective rib 15, 20, as illustrated in FIG. 8A. For example, the axis Z of the hole 105 may define an angle β with the axis Y, and, in some cases, the angle β may be between approximately 5° and approximately 50°, such as between approximately 25° and approximately 35°. The angle β of one or more of the holes 105 may be selected so as to provide a fastener to be inserted into the hole a greater length over which to engage the rib bone 15, 20 underlying the reinforcing member 101, 102, without compromising the structural integrity of the bone in the region in which the fastener is inserted (e.g., by selecting too shallow of an angle β).

Furthermore, in embodiments in which the extended region 140 defines closure holes 160 (as shown in FIG. 5), the closure holes may be angled with respect to an axis Y perpendicular to a surface of the respective rib 15, 20, as illustrated in FIG. 8B. The axis Z of the hole 160 may, for example, define an angle Θ with the axis Y that is between approximately 5° and approximately 50°, such as between approximately 25° and approximately 35°. In the case of the closure holes 160, the angling of the closure holes may serve to guide the closure members 130 away from the neurovascular bundles, such as when the closure holes are provided in the reinforcing member 102 to be applied to the lower rib 20.

Having described the components of the system and their interaction with each other and the patient's ribs, a method of supporting a pair of ribs will now be described. According to the method, a first reinforcing member may be attached to an outer surface of a first one of a rib pair, such as via fasteners (e.g., self-locking bone screws) as described above. A second reinforcing member may be attached to an outer surface of a second one of the rib pair such that each reinforcing member is laterally disposed on an opposite side, with respect to the other reinforcing member, of an intercostal space that extends between the ribs of the rib pair. One or more closure members may then be extended between the rib pair and the reinforcing members attached thereto, and the ends of each closure member may be secured with respect to the reinforcing members to approximate the ribs.

As described above, at least one of the first reinforcing member or the second reinforcing member may comprise at least one extended region and at least one connecting portion. The extended region may include a lateral edge extending away from a midline of the respective reinforcing member, and at least one of the closure members may be wrapped around or otherwise engaged with the lateral edge of the extended region so as to clear a neurovascular bundle associated with the respective one of the rib pair. In this way, discomfort to the patient during healing may be minimized, as described above. In some embodiments, at least one of the closure members may be wrapped around a scalloped edge of the connecting portion, wherein the scalloped edge is configured such that the respective closure member makes no contact with the corresponding edge of the respective one of the rib pair.

The particular method of attachment of the reinforcing members and approximation of the ribs will depend on the patient's anatomy, the extent of chest reconstruction needed, the overall medical condition of the patient, the preferences of the practitioner, and other considerations. For example, in some embodiments, the reinforcing member may be bent by the surgeon so as to have a curvature that more closely conforms to the natural curvature of the ribs in the location to which the reinforcing member is to be applied. Moreover, although embodiments are described and illustrated in which two reinforcing members are applied to a rib pair that has two adjacent ribs, in some cases a single reinforcing member may be used individually, such as on a lower one of a pair of ribs when a closure member is used or on any rib without the use of closure members. In addition, in some cases, reinforcing members may be applied to a rib pair that has two nonadjacent ribs, such as a $2^{nd}$ rib and a $4^{th}$ rib on the same side of the sternum. In such cases, closure members may be used that extend from the lower rib (e.g., the $4^{th}$ rib) to the upper rib (e.g., the $2^{nd}$ rib), where an intermediate rib (e.g., the $3^{rd}$ rib in this example) may be disposed between the upper and lower ribs and may have no reinforcing members.

Furthermore, in some embodiments, the reinforcing members 101, 102 shown in FIG. 3 may have the same structure, where the reinforcing member 102 to be applied to a lower one of the rib pair may be arranged such that the lateral edge 141 of the extended region 140 is extended down (e.g., away from the upper rib) so as to provide clearance for the corresponding neurovascular bundle. Thus, in such embodiments, the first and second reinforcing members 101, 102 may be mirror images of each other, with one rotated 180° from the other for attachment to the ribs. In other cases, however, different lengths and configurations of reinforcing members (e.g., reinforcing members having a different number of extended regions) may be used for the upper and lower ribs.

In still other embodiments, only the lower of the rib pair may have attached thereto a reinforcing member with extended regions as described above. The upper of the rib pair may, rather, have attached thereto a reinforcing member with no extended regions, as there is typically no neurovascular bundle along the upper edge of the upper rib that the closure member would contact.

Moreover, in some embodiments, one or both reinforcing members may be arranged such that the medial end 175 of the reinforcing member 101, 102 can be fastened to the sternum via one or more of the holes 105. This may be the done, for example, when there is broken or mangled cartilage joining the particular rib to the sternum or to treat conditions such as costochondral separation.

In still other embodiments, reinforcing members may be applied to ribs in preparation for performing a thoracotomy as support for the ribs and to minimize the pain associated with rib spreading. For example, reinforcing members may be fastened to two adjacent ribs before the ribs are spread to prevent or reduce fracturing of the ribs during the thoracotomy. Upon completion of the thoracotomy, closure members may be applied to the ribs with the implanted reinforcing members to approximate those ribs and promote healing.

Although closure members 130 comprising wires or sternal sutures are described above, in other embodiments, the reinforcing members 101, 102 may be used with other kinds of closure members. With reference to FIG. 9, for example, in some embodiments, a system for supporting ribs is provided in which the reinforcing members 101, 102 are configured to receive closure members 200 that, when installed, extend only between the reinforcing members on one side of the ribs (e.g., an outer side of the ribs) as opposed to looping around the ribs to extend both along an outer side of the ribs and along an inner side of the ribs. Use of closure members 200 instead of closure members 130 (shown in FIG. 4), which may be metal wires, cables, or sternal sutures, as described above, that must be looped around the ribs and have their ends twisted together to form a closed loop, may be less invasive to the patient. This is because passing a closure member 130 between and under the ribs generally requires the surgeon to cut through tissue and makes contact with nerve bundles more likely. Extending closure members such as the closure member 200 along only the exterior surface of the ribs, however, avoids insertion of the closure member ends in the intercostal space, as described in greater detail below.

Accordingly, as shown in the embodiments of FIGS. 9 and 10, for example, in some cases closure members 200 are provided that comprise two opposing attachment ends (e.g., a first attachment end 205 and a second attachment end 206) and a main body 210 extending therebetween. One or both of the attachment ends 205, 206 may be configured to engage a corresponding reinforcing member 101, 102 via a respective extended region 140, such as by being attached to a respective receiving member of the corresponding reinforcing member. The receiving member may, for example, be a hole as depicted in FIGS. 9 and 10, such as the closure hole 160 shown in FIG. 5 and described above. Thus, in the depicted embodiment, the attachment end 205, 206 may be configured to be passed through the hole of the receiving member 160, as shown. In other cases, however, the receiving member may be a recess, a notch, a protrusion, or any other feature, and the attachment end 205, 206 of the closure member 200 may be correspondingly configured to attach to or otherwise engage the recess, notch, or protrusion.

The main body 210 may be configured to bias the attachment ends towards each other so as to approximate the respective rib pair 15, 20 to which the reinforcing members 101, 102 are attached (e.g., via fasteners, not shown). For example, the main body 210 may comprise a material, such as nitinol, titanium, or other biocompatible metal or material, that can be formed (e.g., shaped) so as to have a spring-like tendency to pull the two attachment ends towards each other. In this way, when the closure member 200 is installed (e.g., engaged with reinforcing members 101, 102 that are attached to a rib pair 15, 20), the built-in tension of the main body 210 may facilitate stabilization of the ribs 15, 20 of the rib pair by holding the rib pair generally in place with respect to one another and keeping them from moving in a way that might otherwise be destructive to the healing process, such as when the rib cage expands due to breathing.

In some embodiments, for example, the main body 210 of the closure member 200 may comprise an expansion feature 220 that is configured to allow a distance between the pair of ribs 15, 20 to increase and decrease due to respiration while still biasing the first and second attachment ends 205, 206 towards each other. As shown in FIGS. 14A and 14B, for example, the expansion feature 220 may be a spring portion formed integrally with the main body 210, such as an arched portion as depicted or a spring coil. Prior to installation, as shown in FIG. 14A, the expansion feature 220 of the closure member 200 may have a predefined shape with a distance $d_e$, corresponding to a distance $d_{cm}$ across which the closure member extends at rest. Following installation, such as after the attachment ends 205, 206 of the closure member 200 have been engaged with the reinforcing members 101, 102 and the closure member extends between two ribs 15, 20 of a rib pair, the expansion feature 220 may be pulled, or expanded, by tensile forces transmitted via the engagement of the attachment ends 205, 206 that are applied each time the rib cage expands (e.g., when the patient takes a breath). The resulting distance $D_e$ defined by the expansion feature 220 (FIG. 14B) corresponding to the expanded distance $D_{cm}$ across which the closure member extends may thus be larger than the original distance $d_e$ of the expansion feature ($D_e > d_e$). In other words, the spring-like properties of (at least) the expansion feature 220 may allow the main body 210 to expand and contract with expansion and contraction of the rib cage without breaking or otherwise damaging the closure member 200 or the bone to which the corresponding reinforcing members 101, 102 are attached.

Referring now to FIGS. 11-13A, the closure members 200 may be configured in various ways to allow the attachment ends 205, 206 to be secured to the corresponding reinforcing members 101, 102. For example, as illustrated in FIG. 11, in some embodiments (e.g., where the receiving members comprise holes), at least one of the first or second attachment ends 205, 206 may be configured to allow a free end 208 of the respective attachment end to be passed through the hole and wrapped around another portion 209 of the respective attachment end so as to secure the respective attachment end to the corresponding reinforcing member. In this regard, once the free end 208 of the attachment end 205, 206 has been passed through the hole of the receiving member 160, the free end may be wrapped around the lateral edge 141 of the extended region 140 of the reinforcing member 101, 102 by the surgeon and twisted back onto a portion 209 of the closure member 200 on the other side of the receiving member.

In this way, in some embodiments, at least one of the first or second attachment ends 205, 206 may be configured to be secured to the corresponding reinforcing member 101, 102 so as to adjust a length $L_{cm}$ of the closure member 200 as measured from an engagement point 215 of one attachment end 205 with the corresponding reinforcing member 101 to an engagement point 216 of the other attachment end 206 with the corresponding reinforcing member 102. For example, if the surgeon while installing the closure member 200 decides that a shorter length $L_{cm}$ would be appropriate or that more tension should be applied between the two engaged ribs 15, 20, the surgeon may pull more of the closure member through the receiving member 160 and may, for example, wrap the free end 208 about a portion 209 of the closure member farther away from the free end, or otherwise secure the attachment end, as described below, so as to maintain a shorter length $L_{cm}$ of the closure member. Conversely, if the surgeon decides that a longer length $L_{cm}$ would be appropriate or that less tension should be applied between the two engaged ribs 15, 20, the surgeon may pass less of the closure member through the receiving member 160 and may, as a result, wrap the free end 208 about a portion 209 of the closure member that is closer to the free end, or otherwise secure the attachment end, as described below, so as to maintain a longer length $L_{cm}$ of the closure member.

In some embodiments, rather than requiring the closure member to be manually twisted onto itself, one or both of the attachment ends 205, 206 may comprise a locking feature. With reference to FIGS. 12 and 12A, for example, the locking feature 230 may be configured to receive a free end 208 of the respective attachment end in a first direction D1 and to prevent movement of the free end in a second direction D2 so as to secure the respective attachment end to the corresponding reinforcing member 101, 102. The locking feature 230 may, for example, comprise teeth 235 that are configured (e.g., sized and shaped) to engage corresponding teeth 240 formed proximate the free end 208 of the attachment end 205. The teeth 235 may, for example, comprise guiding surfaces 236, which may be angled to allow corresponding surfaces 242 of the teeth 240 to slide along them in the first direction D1 from one locked position (e.g., a position between adjacent pairs of teeth) to the next, in a ratchet-type manner. Once in a locked position, however, movement in the second direction D2 would cause locking surfaces 237 of the teeth 235 to engage corresponding surfaces 243 of the teeth 240, thereby preventing movement in the second direction D2. In some cases, selection of a locked position (e.g., how far the free end 208 is advanced with respect to the teeth 235 of the locking feature 230) may allow the surgeon to adjust the length of the closure member, as described above with respect to FIG. 11. Moreover, in some embodiments, the closure members 200 may be coated with a polymer material, and in some cases the teeth 235, 240 may be comprised of a polymer material. Thus, in some cases, the teeth may be formed integrally with the polymer coating.

In still other embodiments, at least one of the first or second attachment ends 205, 206 may define threads that are configured to engage corresponding threads of a fastener. In this regard, engagement of the fastener with the at least one of the first or second attachment ends 205, 206 may serve to secure the respective attachment end to the corresponding reinforcing member 101, 102. For example, the dimensions of the fastener may be such that the fastener is too large to pass through the receiving member (e.g., the hole 160). Thus, after the threaded attachment end 205, 206 is passed through the receiving member (160 in the depicted embodiment), the fastener may be threaded onto the attachment end (e.g., to an appropriate extent considering the length of the threaded portion and the total desired length of closure member, for example, as measured from engagement point to engagement point). In some cases, for example, approximately 4-6 cm of threads may be provided at one or both attachment ends 205, 206. Moreover, a position along the threads to which the fastener is advanced may allow the surgeon to adjust the length of the closure member, as described above with respect to FIG. 11 (e.g., engaging more threads to shorten the closure member and vice versa). Furthermore, in some cases, the fastener may be threaded onto the attachment end 205, 206 such that removal of the fastener is either not possible or requires special tools or procedures (e.g., via use of thread locking fluid or a locking nut).

In some cases, with reference to FIGS. 13 and 13A, one of the first or second attachment ends (such as the second attachment end 206, as shown) may comprise an anchor 250 configured to engage the corresponding reinforcing member 102. The anchor 250 may, for example, be an enlarged portion on the end of the attachment end 206 that is configured (e.g., sized and shaped) such that the anchor cannot pass through the receiving member 160. For example, the anchor 250 may be configured to have a diameter, length, and/or width that is greater than that of the receiving member (e.g., greater than the diameter of the closure hole 160 in the depicted embodiment). In still other cases, the anchor 250 and/or the receiving member may be shaped such that the anchor fits into the receiving member, but does not pass through (e.g., like a plug). The anchor 250 may, in some cases, be formed integrally with the attachment end 205, 206.

Thus, to engage the closure member 200 with the reinforcing members 101, 102 in the depicted embodiment of FIG. 13, the first attachment end 205 may be passed through the receiving member defined in the second reinforcing member 102 (e.g., threaded through the hole 160 from an inner side of the reinforcing member) and extended from the second reinforcing member to the first reinforcing member 101 along an outer side of the reinforcing members. The first attachment end 205 may then be passed through the receiving member defined in the first reinforcing member 101 from the outer side to the inner side of the first reinforcing member. As described above, the first attachment end 205 may then be wrapped around the lateral edge 141 and engaged with a portion of the closure member 200 on the other side of the receiving member 160 to secure the closure member in place, such as via wrapping or the locking feature 230 described above with reference to FIGS. 12 and 12A. In this way, the closure member 200 may be held in place at one end by the anchor 250 and at the other end via another permanent or reversible mechanism, such as the locking feature 230.

Closure members 200 as described above with respect to FIGS. 9-14A may be configured in various ways, as described above, and may come in a variety of lengths and thicknesses. In some cases, for example, the nominal length of the closure member (e.g., the length from one engagement point to the other) may be between approximately 1 and 20 cm, such as between approximately 4 and 8 cm. The thickness or diameter of the closure members 200 may similarly range from approximately 1 to 6 mm or more. In some cases, the closure members 200 may come in multiple discrete sizes, such as small (e.g., 4 cm long) and large (e.g., 8 cm long).

Many modifications and other embodiments of the invention will come to mind to one skilled in the art to which this invention pertains having the benefit of the teachings presented in the foregoing descriptions and the associated drawings. For example, although the extended regions 140 are depicted in the figures as having a rounded lateral edge and a rounded inner edge (e.g., in the form of an arch), in some embodiments the extended regions may extend away from the midline M in an angular fashion, so as to have a square, rectangular, or trapezoidal profile, for example. With reference to FIGS. 15-17, example reinforcing members are illustrated that include extended regions having an arch shape in which both the lateral edge 141 and the inner edge 142 are rounded (FIG. 15), an oblique M-shape in which both edges 141, 142 have an oblique M shape (FIG. 16), and a three-sided arch shape in which the lateral edge 141 has three sides in a rectangular form and the inner edge 142 has a rounded, arch shape (FIG. 17). Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A system for supporting a pair of ribs comprising:
   first and second reinforcing members, each reinforcing member configured to be placed on an outer surface of a respective one of a rib pair such that each reinforcing member is laterally disposed on an opposite side, with respect to the other reinforcing member, of an intercostal space that extends between the ribs of the rib pair, wherein at least one of the first reinforcing member or the second reinforcing member comprises at least one extended region and at least one connecting portion, wherein the extended region includes a lateral edge extending away from a midline of the respective reinforcing member, wherein the at least one connecting portion defines a plurality of holes;
   a plurality of fasteners, wherein each hole of the at least one connecting portion of the first and second reinforcing members is configured to receive one of the fasteners so as to secure a respective reinforcing member to a corresponding rib, and
   a plurality of closure members, each closure member being configured to be extended between the respective rib pair and the first and second reinforcing members secured thereto so as to approximate the respective rib pair, and each closure member comprising a closure wire configured to be wrapped around the respective rib pair and the first and second reinforcing members secured thereto so as form a closed loop;
   wherein each extended region is configured to receive a portion of a corresponding closure member, and
   wherein the lateral edge of the extended region of the at least one of the first reinforcing member or the second reinforcing member is configured to clear a neurovascular bundle associated with the respective one of the rib pair so as to minimize discomfort to the patient during healing.

2. The system of claim 1, wherein the extended region comprises at least one groove configured to receive the portion of the respective closure member therein.

3. The system of claim 1, wherein the extended region comprises at least one receiving member configured to receive the portion of the respective closure member.

4. The system of claim 1, wherein each closure member comprises two opposing attachment ends and a main body extending therebetween, wherein each attachment end is configured to engage a corresponding reinforcing member via a respective extended region and the main body is configured to bias the attachment ends towards each other so as to approximate the respective rib pair.

5. The system of claim 1, wherein the extended region of the reinforcing members is an arched region, and wherein the lateral edge is rounded.

6. The system of claim 1, wherein at least one of the first reinforcing member or the second reinforcing member comprises absorbable material.

7. A method of supporting a pair of ribs comprising:
   attaching a first reinforcing member to an outer surface of a first one of a rib pair;
   attaching a second reinforcing member to an outer surface of a second one of the rib pair such that each reinforcing member is laterally disposed on an opposite side, with respect to the other reinforcing member, of an intercostal space that extends between the ribs of the rib pair;
   applying a plurality of closure members to the reinforcing members, wherein at least one of the first reinforcing member or the second reinforcing member comprises at least one extended region and at least one connecting portion, wherein the extended region includes a lateral edge extending away from a midline of the respective reinforcing member, and wherein at least one of the closure members is applied to the lateral edge of the extended region so as to clear a neurovascular bundle associated with the respective one of the rib pair and minimize discomfort to the patient during healing; and
   securing ends of each closure member with respect to the reinforcing members to approximate the ribs.

8. The method of claim 7, wherein each closure member comprises two opposing attachment ends and a main body extending therebetween, wherein the method further comprises engaging each attachment end with a corresponding reinforcing member via a respective extended region such that the closure members extend between the ribs of the rib pair on an outer side of the ribs, only, with the main body configured to bias the attachment ends towards each other so as to approximate the respective rib pair.

9. The system of claim 1, wherein at least one of a lateral end or a medial end of at least one of the first reinforcing member or the second reinforcing member is angled away from the midline of the respective reinforcing member.

10. The reinforcing member of claim 1, wherein the extended region comprises at least one closure hole configured to receive a portion of a respective closure member therethrough.

11. The method of claim 7, wherein the closure members comprise closure wires, wherein the method further comprises wrapping the closure members around the respective rib pair and the first and second reinforcing members secured thereto so as to form a closed loop.

* * * * *